United States Patent [19]

Herold et al.

[11] Patent Number: 5,702,362
[45] Date of Patent: Dec. 30, 1997

[54] NASAL APPLICATOR

[75] Inventors: Heiko Herold, Neuss; Axel Wollenschläger, Bergisch Gladbach; Alfred von Schuckmann, Kevelaer, all of Germany

[73] Assignee: Bayer Aktiengesellschaft, Leverkusen, Germany

[21] Appl. No.: 646,828

[22] Filed: May 21, 1996

[30] Foreign Application Priority Data

May 26, 1995 [DE] Germany .................. 195 18 810.1

[51] Int. Cl.⁶ .................................................. A61M 13/00
[52] U.S. Cl. .................................... 604/58; 604/48; 604/73
[58] Field of Search .............................. 604/57, 58, 73, 604/48; 128/203.15, 203.21, 203.24

[56] References Cited

U.S. PATENT DOCUMENTS

| | | | |
|---|---|---|---|
| 4,534,345 | 8/1985 | Wetterlin | 604/58 |
| 4,596,343 | 6/1986 | Ford, Jr. | |
| 5,113,855 | 5/1992 | Newhouse | 128/203.15 |
| 5,312,331 | 5/1994 | Knoepfler | |

FOREIGN PATENT DOCUMENTS

| | | | |
|---|---|---|---|
| 27620 | 2/1907 | Austria . | |
| 0518087 | 12/1992 | European Pat. Off. . | |
| 2850386 | 5/1980 | Germany . | |
| 9107574 | 9/1991 | Germany . | |
| 4211475 | 6/1993 | Germany . | |
| 8908470 | 9/1989 | WIPO . | |
| 9204066 | 3/1992 | WIPO | 604/58 |
| 9426338 | 12/1993 | WIPO | 604/58 |
| 9106333 | 5/1995 | WIPO | 604/58 |

*Primary Examiner*—Michael Powell Buiz
*Assistant Examiner*—N. Kent Gring
*Attorney, Agent, or Firm*—Sprung Kramer Schaefer & Bruscoe

[57] ABSTRACT

Nasal applicators are an important aid for introducing powdery, pharmacologically active medicaments into the nasopharyngeal space of a patient. The present nasal applicator is based on a manually actuated compressed air source connected to an inflow channel (8) for generating a compressed air jet, a storage container (3) for the medicament and a metering device for making available a portioned-off quantity of the medicament which is caught by the compressed air jet and transported through an outflow channel (9) into the nose. The metering device consists of a metering drum (5) in which the storage container (3) for the medicament is formed by the interior of the metering drum (5). In addition, the inflow channel (8) is connected to one end of a metering channel (7) and the outflow channel (9) to the other end of the metering channel (7). The quantity of medicament made available in one portioning chamber (13) of the metering drum (5) protrudes into the metering channel (7) in such a manner that it is completely caught by the compressed air jet and transported into the nasal cavities.

8 Claims, 4 Drawing Sheets

NASAL APPLICATOR

The invention relates to a device for introducing a powdery medicament into the nose.

Powdery medicaments are used for treating inflammatory and allergic diseases of the nasal mucosa.

In addition to this, nasal inhalation is also possible for certain active substances which are to be administered systemically (e.g. short-chain peptides). In this way, the injections which patients find unpleasant are in many cases avoided.

Some of the appliances which have been developed for nasal administration of powders contain the active substance in portioned-off form in hard gelatin capsules, which have to be loaded into the inhaler appliance and opened up immediately prior to inhalation.

This loading procedure is awkward and cannot be done satisfactorily by elderly people with rheumatic symptoms or poor eyesight.

To overcome this drawback, a self-metering appliance has been developed (German Offenlegungsschrift 2,529, 522) in which the awkward loading procedure is dispensed with. A disadvantage of this appliance, however, is that the patient has to take the powder up by means of active inhalation. It is not possible to do this satisfactorily, especially when the mucous membranes are swollen.

In order to blow the active substance actively into the nose, appliances have also been developed in which the active substance is present in dissolved or suspended form in a pressure-liquefied propellent gas. On actuating the metering valve, a portioned-off quantity of the active substance suspension is released. The propellant which is under inherent vapour pressure evaporates immediately, disperses the active substance and blows into the nasal orifice. A disadvantage of this method of administration lies in the use of pressure-liquefied propellants which additionally have to be taken up by the patient's body. Further auxiliaries such as, for example, valve lubricants, antiflocculating agents etc., often have to be added to the formulations. Finally, the propellants used in the pharmaceuticals sector are also criticized because of their damaging influence on the environment (e.g. contribution to warming of the earth's atmosphere and/or destruction of the ozone layer).

The object set was to develop a user-friendly, self-metering inhaler appliance which manages without using pressure-liquefied propellants and which blows the active substance actively into the nasal cavity.

This object is achieved by the invention as specified in claim 1.

The claims subsequent thereto represent further advantageous embodiments of the device according to the invention.

As a result of such a configuration, a device of the generic type is obtained which is of a simplified structure and of improved usefulness and safety. The mechanical outlay is greatly reduced. The quantity is brought into the position ready for delivery at rest. The user can concentrate on introduction of the active substance. In concrete terms, the applicator is designed, according to the invention, such that the metering arrangement consists of a metering drum in which the storage container for the medicament is formed by the interior of the metering drum, such that the inflow channel is connected to one end of the metering channel, and the outflow channel is connected to the other end of the metering channel, and such that the quantity of medicament which has been made ready in a portioning aperture of the metering drum protrudes into the metering channel. The interior of the metering drum is now used for forming the reservoir. Its content is kept in motion. This content passes by the shortest route into the standby position ready for delivery. Discharging takes place there, with no residues remaining behind. Because of the stated orientation and sequence of the functional areas, no particles can fall back. The compressed air strikes in the first instance against the quantity of medicament and flows into the exactly positioned and portioned-off, exposed heap of the medicament. The dome-shaped zone presented is rapidly carded off, swirled or dispersed, and, upon actuation of the compressed air source, is administered to the target site. The medicament is blown counter to the effect of gravity. Incorrect holding is ruled out in practice, since the position of the metering drum suggests the correct handling, and the outflow channel lying at the other, upper end, with the applicator nozzle as transfer bridge, is easily recognizable to the user. In addition, there is no potential risk of an overdosage forming; a quantity of powder which has not been administered disappears in the direction of the reservoir. It is not added to in the next cycle. As regards the design of the metering drum, this is configured in such a manner that it has a rotary sleeve equipped with portioning apertures. The portioning apertures arranged at a uniform angular distribution dip into the powder reservoir as a remit of the mixing-drum-like rotation of the metering drum, without pressing etc. occurring. The metering gives the correct volume, including the penultimate portion and, if appropriate, right up to the final portion. Also, as a result of using the drum movement, the medicament does not agglomerate. It is furthermore proposed that the rotary sleeve is formed by the circumferential wall of a pot whose base has a mining knob. With respect to the rotary mounting of the metering drum, and as regards obtaining quantities of medicament for inhalation which are always the same, it proves advantageous if the rotary sleeve enclosed by an outer wall is underpinned over a partial angular range by an inner wall section, which forms the base of the portioning chamber formed in each case by one of the apertures. In this connection, it is also advantageous that the transverse walls of the apertures extend in a trapezoidal shape or wedge shape towards the center of the metering drum. This leads, as regards the transverse walls, to a convexly curved, trapezoidal trough as compartment chamber, directed to the apex of a V, in other words directed upwards. A further improvement, which is especially favourable from the point of view of production technology, lies in the fact that all the air channels are incorporated in a support structure which can be enclosed by two housing shells and in which the metering drum is also mounted, and the housing shells form the cover for the air channels. It can also be provided for the support structure to form a stand for the device when designed as a standing appliance, the shoulder forming an engagement limit stop for the protective cap.

The following additional advantages are achieved by the invention:

The applicator is also suitable for medicament formulations which have poor flow properties or which tend to cake. As a result of the simultaneous homogenization upon each metering operation, any powder bridges which may be present are broken up and loosened.

It has also been found that the metering accuracy is not appreciably impaired in the event of slight deviations from the prescribed use position; i.e. slight deviations from the use position are not critical with regard to the metering accuracy. After the metering, i.e. after actuation of the metering drum, the inhalation can take place in any desired position.

On account of the construction being amenable to injection-moulding, and on account of the small number of components required, the applicator can be manufactured cost-effectively and economically in large piece numbers.

The subject matter of the invention is explained in greater detail hereinafter with reference to an exemplary embodiment which is illustrated in the drawing, in which.

Figure 1:
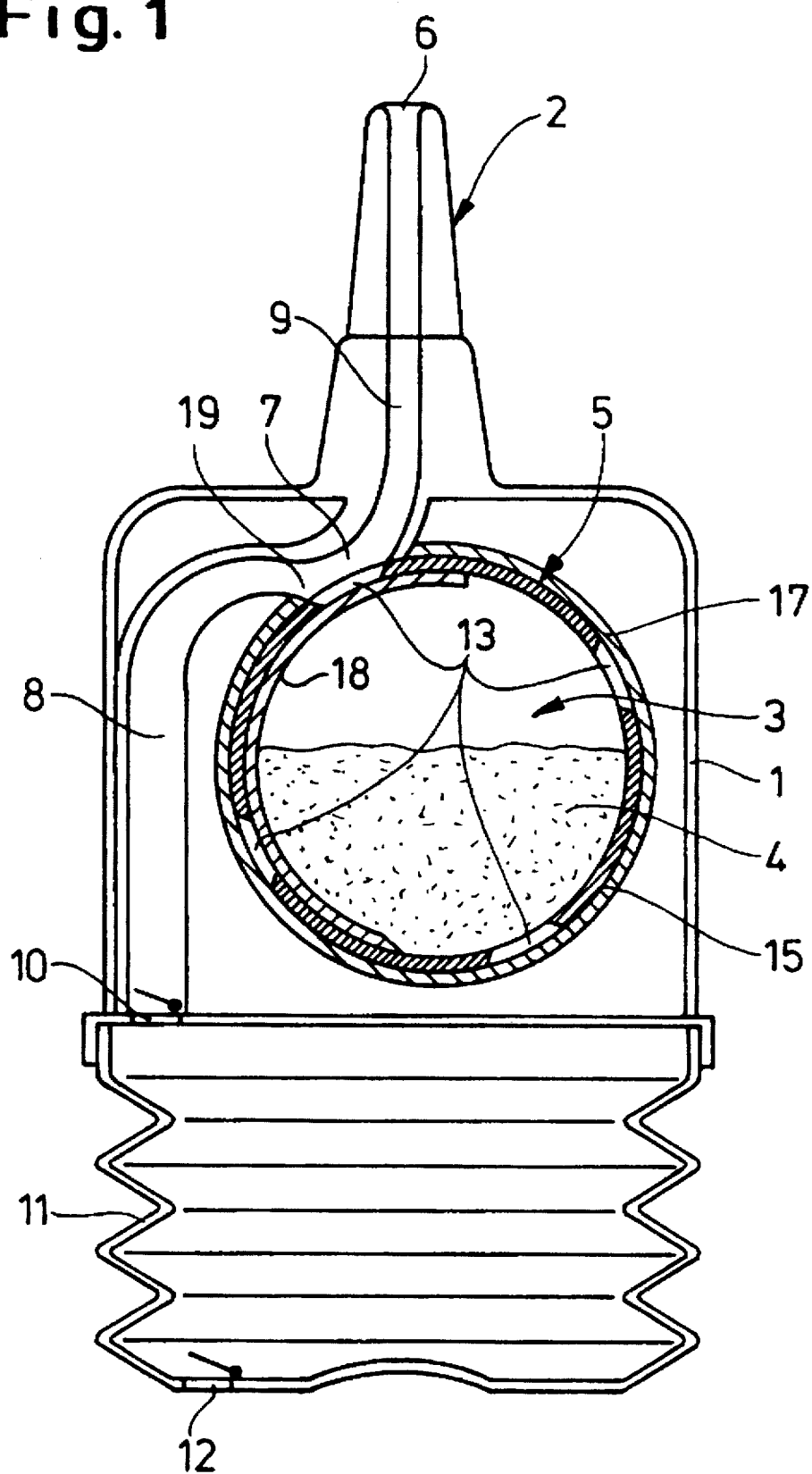
FIG. 1 shows a plan view of the nasal applicator.
Figure 2:
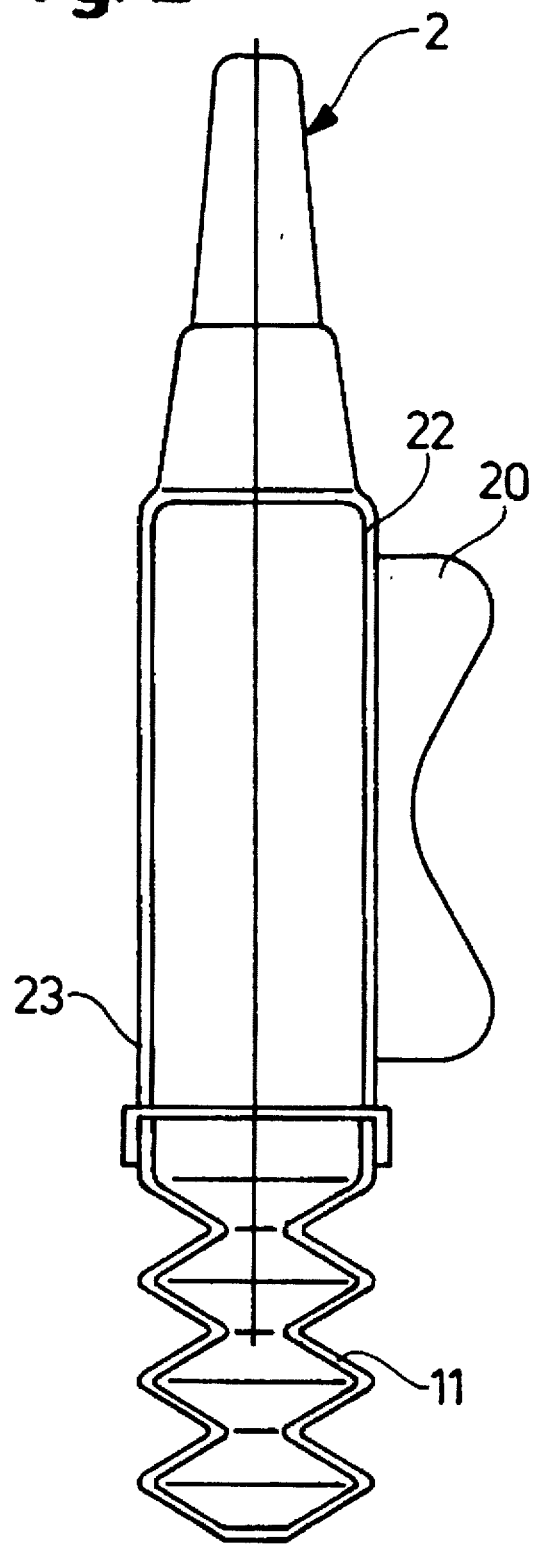
FIG. 2 shows a side view.
Figure 3:
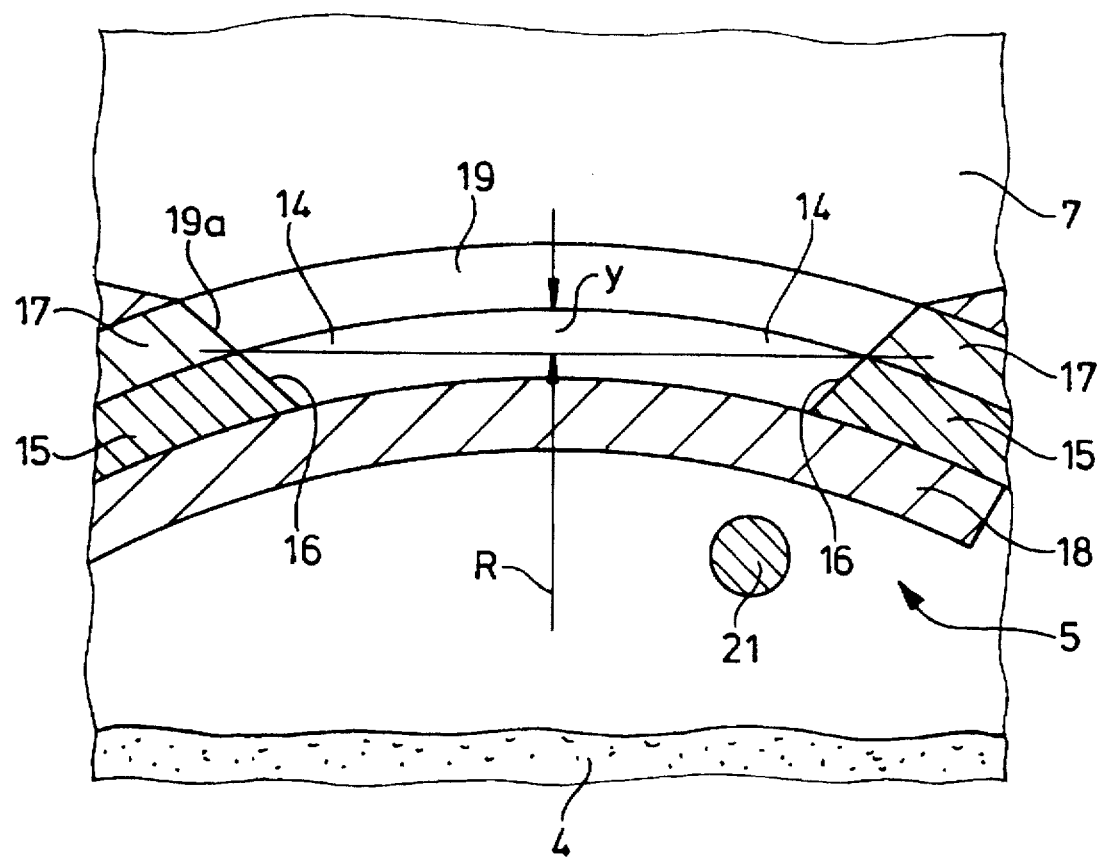
FIG. 3 shows a detail of the metering device in cross section.
Figure 4:
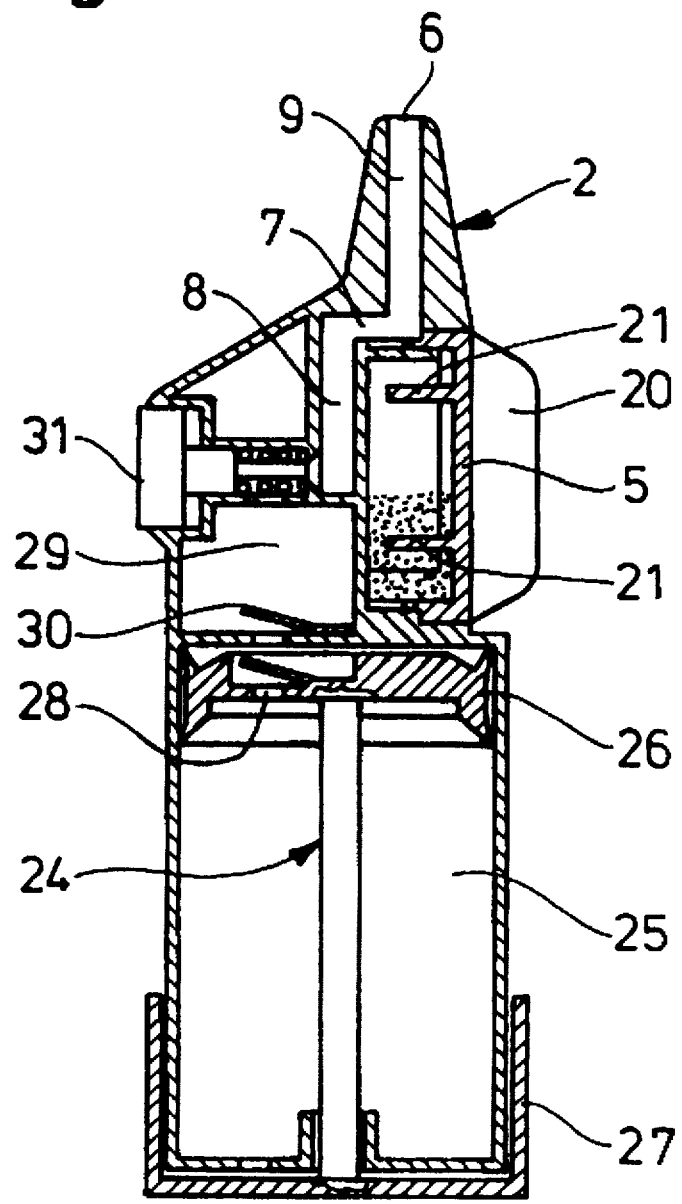
FIG. 4 shows a plan view of a modified embodiment of the nasal applicator.

The pocket-size device, hereinafter called the applicator, has, in accordance with FIGS. 1 and 2, a long rectangular, pocket-size, flat housing 1. Its head area includes a so-called nasal applicator 2. In the description below, it is assumed that the applicator is located in a vertical plane which corresponds to the plane of projection in the figures.

The applicator includes a storage container 3 which is filled with powdery medicare cut 4 (formulation).

The storage container 3 is formed by the interior of a metering drum 5. The metering drum 5 is mounted rotatably in the housing 1 and can be actuated directly from the outside by hand. It is located in the foot area of the applicator and in terms of volume uses up almost the entire width of the housing 1.

When it is being used, the applicator is held in such a way that the metering part is at the bottom and the adapter piece 2 with the applicator opening 6 is at the top (use position). This position also corresponds to the representation chosen in FIG. 1 and FIG. 2.

When the applicator is in the use position, the metering drum 5 and adapter piece 2 thus in practice lie vertically one above the other. The powder particles are thus conveyed from the bottom upwards during application.

The basic function of the metering drum 5 consists in that, during a metering operation, a defined quantity of medicament is brought from the storage container 3 into a metering channel 7, by rotating the drum, and is conveyed from there, by means of a pulsed flow of air, through the applicator opening 6 and into the nose. For this purpose, the metering channel 7 is connected on the one hand to an inflow channel 8 and on the other hand to an outflow channel 9 which leads to the applicator opening 6 in the nasal adapter piece 2. The inflow channel 8 is connected via an outlet valve 10 to a concertina bellows 11. Also arranged on the concertina bellows 11 is an inlet valve 12. By actuating the concertina bellows 11 (compression), an air jet is generated which flows via the inflow channel 8 into the metering channel 7 and there expels the quantity of medicament, which has been made ready, through the adjoining outflow channel 9 and through the applicator opening 6 into the patient's nose. Thus, in the metering channel 7, the precisely metered quantity of powder which has been removed from the storage container 3 is exposed to the compressed air jet and expelled.

For this purpose, the metering drum 5 has portioning chambers 13 which are open on the channel side. As a result of the circular curvature of the metering drum 5, the portioned-off medicament (formulation) is made ready in the metering channel 7 as a forwardly bulging layer. The resulting dome of medicament can be cleared off and out with particularly favourable flow characteristics. The convex curvature of the domes of medicament can be seen particularly clearly from FIG. 3. There, the additional height y (seen in the chord center) resulting from the curvature of the portioning chamber 13 is easily discernible from the radials R directed at the center of the metering drum 5. The center lies on the geometric axis of rotation of the metering drum 5.

As can be seen from FIG. 1, and in particular from FIG. 3, a portioning chamber 13 is formed by an aperture 14 in a rotary sleeve 15 of the pot-shaped metering drum 5. According to FIG. 1, four apertures 14 or portioning chambers 13 are distributed uniformly around the circumference of the rotary sleeve 15. The apertures 14 are delimited by side walls 16 which are bevelled in such a way that the apertures 14 taper towards the center of the metering drum 5. The bevel angle lies at 45° to the shortest connection between the outer surface and inner surface of the metering drum wall. The transverse walls 16 give the portioning chamber 13 the shape of a trapezoidal, outwardly opening, curved trough which is of considerably greater length than width.

The rotary sleeve 15 is mounted rotatably between an annular wall 17 and a likewise annular wall section 18 which extends over an arc angle of approximately 180°. The approximately semicircular, web-shaped wall section 18 is here arranged in such a way that it on the one hand forms the base area of the metering channel 7 and at no point is there a continuous connection between the air channels 8 and 9 and the storage container 3, and, on the other hand, at the lower end leaves the foot zone of the rotary sleeve 15 free (see FIG. 1). The annular wall 17 and the wall section 18 are formed integrally on the housing 1. The mounting of the rotary sleeve can be improved by means of a beating collar which is approximately 1 to 2 mm high and which extends, as a continuation of the said wall section 18, over the remaining circumferential angle and is similarly formed integrally on the housing 1. In this way, the circumferential surface of the rotary sleeve 15 is guided with precision rotation in the annular gap between the annular wall 17 and the wall section 18 including the said bearing collar. The annular wall 17 has an inlet window 19 facing the metering channel 7. The side surfaces 19*a* of the inlet window 19 are bevelled in such a way that they are flush with the side surfaces 16 of the portioning chamber 13 when the portioning chamber 13 is located exactly under the inlet window 19. As long as a portioning chamber 13 is located within the angle range of the wall section 18, the outer surface of the wall section 18 functions as a base for the trough-shaped portioning chamber 13. For this reason, the height of the web-shaped wall section 18 is dimensioned slightly greater than the width of the aperture 14. Upon a further rotation of the rotary sleeve 15 in the clockwise direction, i.e. after the portioning chamber 13 under the inlet window 19 has advanced beyond the tight, upper end of the wall section 18, the base of the portioning chamber 13 is open, so that it once again communicates with the storage container 3.

The said wall section 18 in the area of the metering channel 7 functions with its outer surface as base, whereas in the region of the ascending portioning chamber, leading in the clockwise direction, it shields from the storage container on the inside the quantity of powder, taken from the powder reservoir, of the next aperture 14. In FIG. 1 this portioning chamber is located at an "8 o'clock position", while the portioning chamber ready for inhalation is at an "11 o'clock position". The loading of a portioning chamber 13 is effected by means of the associated aperture 14 being pushed forwards under the powder reservoir 4 upon further rotation of the rotary sleeve 15 (in FIG. 1 roughly in a zone of from "4 o'clock" to "6 o'clock"), whereupon this portioning chamber 13 fills with the powder. Upon further rotation of the rotary sleeve 15, this portioning chamber passes into the ascending region between "6 o'clock" and "9 o'clock". In this region, the inhalation dose is secured in the portioning chamber by the shielding effect of the wall section 18, whose lower end functions as a stripper, so that any excess powder directed inwards is scraped off. An exact dose with reproducible powder density is achieved in this way.

The wall section 18 leaves about 180° open to the interior of the storage container 3. The rotary sleeve 15 acts as a rotary slide. If the metered quantity of powder is not removed, it passes automatically back into the reservoir, in other words the storage container 3, upon further rotation of the metering drum 15. Quantity accumulation is not possible. This important advantage derives from the vertical orientation of the functional elements.

The circumferential wall of the rotary sleeve 15 of the pot-shaped metering drum 5 is provided on the outside with a conveniently accessible turning knob 20 (see FIG. 2 in particular).

A plurality of loosening fingers 21 are arranged on the base of the pot, parallel to the axis of rotation of the metering drum 5 and distributed uniformly about the circumference, the said loosening fingers 21 projecting into the powder reservoir and their radial spacing from the center being chosen such that they scrape across the rear of the wall section 18 during rotation, so that no powder can settle there. Viewed in the clockwise direction, in accordance with FIG. 1, one loosening finger 21 is arranged immediately behind each aperture 14 (leading). Alternatively, or else in addition, the loosening fingers can be arranged stationary on the housing 1, in which case the drum movement is similarly used for loosening the powder.

The applicator housing 1 consists of two housing shells 22 and 23 which are U-shaped in cross-section. The two shells 22 and 23 enclose, in sandwich fashion, a support structure (not shown) as core part, in which there are accommodated, as essential components, the inflow channel 8, the metering channel 7 and the outflow channel 9, as well as a circular recess for mounting the metering drum 5. The air channels 7, 8, 9 are provided for in the form of groove-like depressions of approximately rectangular cross-section and are closed off or covered by the housing shells 22 and 23. This construction guarantees a sufficient mechanical stability, even when the support structure is designed with a relatively thin wall (e.g. about 5 mm) for reasons of reducing weight.

The housing parts 22, 23 can be fastened using a damping technique; an adhesive bonding or thermal bonding is likewise conceivable, unless the complete or partial dismantling of the housing 1 is sought for cleaning purposes or refilling purposes. In this case, the usual traditional means of fastening, such as screw connections, etc., are then to be preferred.

In the modified embodiment of the applicator according to FIG. 4, the compressed air source consists of a manually actuated reciprocating pump 24 which has a pump piston 26 displaceable in a pump chamber 25 and with a hand grip 27 and a valve 28. The pump chamber 25 is connected here to the inflow chamber 8 via a compression chamber 29. At the entrance to the compression chamber 29 (as viewed from the pump chamber) there is an inlet valve 30. By actuating a release button 31 which is pretensioned by means of a spring, the compression chamber 29 can be connected to the inflow channel 8.

The function of the applicators according to FIGS. 1 to 4 will be described again hereinbelow.

According to FIG. 1, the powdery medicament is located inside the rotary sleeve 15 and there reaches into the lower portioning chambers 13. When the rotary sleeve 15 is turned, the filled portioning chamber 13 then first comes between the annular wall 17 and the wall section 18. The portioning chamber 13 can empty only when it is rotated into the region of the metering channel 7, since here the annular wall 17 is interrupted. The user introduces the device via the nasal adapter piece 2 into the nose. By compressing the concertina bellows 11, a volume of air is forced into the metering channel 7 via the pressure valve 10. The portioning chamber 13 standing by is emptied by means of the resulting air jet, and the contents of the chamber are blown into the nose with the flow of air. When the concertina bellows 11 is then released, the pressure valve 10 (outlet valve) closes, while at the same time the inlet valve 12 opens in order to allow air to flow into the concertina bellows 11.

According to FIG. 4, the powdery medicament is again made ready in the rotary sleeve 15, the portioning chambers 13 lying at the bottom filling with the powder. When the rotary sleeve 15 is turned, the powdery medicament is in this case loosened by loosening pins 21 arranged in the sleeve, so as to obtain a good flow. By pushing the pump piston 26 up via the hand grip 27, the air contained in the pump chamber 25 is displaced into the compression chamber 29 via the pressure valve 28 and the inlet valve 30. If a portioning chamber 13 filled with the medicament has been brought beforehand into a standby position in the metering channel 7 by means of actuating the metering drum 5, then the air compressed in the compression chamber is released by means of pressing the release button 31, so that a pulsed flow of air (air jet) flows through the downstream inflow channel 8 at high speed, completely entrains the quantity of powdery medicament standing by in the metering channel and transports it through the outflow channel 9 and the applicator opening 6 into the patient's nose.

We claim:

1. A powdered medication inhaler comprising a manually actuated air source, an inflow channel (8) having two ends, an outflow channel (9) having two ends and a metering channel (7) having two ends, said manually actuated air source being connected to one end of said inflow channel (8), one end of said metering channel (7) being connected to the other end of said inflow channel (8) and the other end of metering channel (7) being connected to one end of said outflow channel (9), the other end of outflow channel (9) comprising an opening for discharging powder out of the inhaler; a metering drum (5), the interior of which comprises a powder storage container (3) and having portioning chambers (13) for metering predetermined quantities of powder from said powder storage container (3) to said metering channel (7) whereby, in operation, the rotation of metering drum (5) causes portioning chamber (13) to remove a predetermined quantity of powder from powder storage container (3) and place it in metering channel (7), and air introduced into inflow channel (8) by said manually actuated air source flows from inflow channel (8) into metering channel (7), entrains said predetermined quantity of powder placed in metering channel (7) by said portioning chamber (13), and carries it through outflow channel (9) and out of the inhaler.

2. An inhaler according to claim 1, wherein the metering drum (5) further comprises a rotary sleeve (15) on the circumference of which the portioning chambers (13) are arranged.

3. An inhaler according to claim 2, wherein the rotary sleeve (15) is formed by the circumferential wall of a pot, on the base of which a turning knob (20) is arranged.

4. An inhaler according to claim 2, wherein the rotary sleeve (15) is enclosed by an annular wall (17) and is underpinned, over a partial angle range, by an inner wall section (18) which forms the base of the portioning chamber (13) formed in each case by an aperture (14).

5. An inhaler according to claim 4, wherein apertures (14) have transverse walls (16) which extend in trapezoidal shape and wedge shape in the direction of the center of the metering drum (5).

6. An inhaler according to claim 2, wherein the channels (7, 8, 9) are accommodated in a support structure which can be enclosed by two housing shells (22, 23) and in which the metering drum (5) is also mounted, the housing shells (22, 23) forming the cover for the channels (7, 8, 9).

7. An inhaler according to claim 1, wherein the air source consists of a concertina bellows (11).

8. An inhaler according to claim 1, wherein said air source is a compressed air source and a compression chamber (29) is arranged between the compressed air source and inflow channel (8), and a release button (31) is arranged between the compression chamber (29) and the inflow channel (8), the air supply stored in the compression chamber (29) being released upon actuation of the release button (31).

* * * * *